United States Patent [19]

Kojima et al.

[11] Patent Number: 6,075,138
[45] Date of Patent: Jun. 13, 2000

[54] **TRANSCRIPTIONAL REGULATORY DNA SEQUENCE ELEMENTS AND SIGNAL PEPTIDE SEQUENCE OF THE *CORIOLUS HIRSUTUS* PHENOLOXIDASE GENE, AND PLASMID VECTORS AND TRANSFORMANTS UTILIZING SUCH SEQUENCES**

[75] Inventors: Yasushi Kojima; Yukio Kita, both of Tokyo; Yukiko Tsukuda, Kashiwa, all of Japan

[73] Assignee: Oji Paper Co., Ltd., Japan

[21] Appl. No.: 08/999,958

[22] Filed: Jan. 15, 1993

Related U.S. Application Data

[63] Continuation of application No. 07/493,031, Mar. 13, 1990, abandoned.

[30] Foreign Application Priority Data

Mar. 14, 1989 [JP] Japan .................................... 1-61859
Mar. 17, 1989 [JP] Japan .................................... 1-65400
Mar. 1, 1990 [JP] Japan .................................... 2-47160

[51] Int. Cl.[7] .......................... C12N 15/67; C12N 15/62; C12N 15/80; C12N 15/81
[52] U.S. Cl. .................. 536/24.1; 536/23.4; 435/69.1; 435/252.3; 435/254.11; 435/254.2; 435/254.21; 435/320.1
[58] Field of Search .............................. 435/69.1, 252.3, 435/254.11, 254.2, 252.21, 320.1; 536/23.4, 24.1

[56] References Cited

U.S. PATENT DOCUMENTS

| H875 | 1/1991 | Ellav et al. ................................ 435/91 |
| 4,695,455 | 9/1987 | Barnes et al. ......................... 424/93 D |
| 5,055,294 | 10/1991 | Gilroy ................................. 424/93 A |
| 5,362,640 | 11/1994 | Tsukamoto et al. ...................... 436/471 |

FOREIGN PATENT DOCUMENTS

| 61-285989 | 12/1986 | Japan ............................. C12N 9/002 |
| 62-220190 | 9/1987 | Japan ............................... C12N 9/42 |
| 2-27985 | 1/1990 | Japan . |

OTHER PUBLICATIONS

Morohoshi, N, et al., 1988, Tokyo Noko Daigaku Nogakaba Enshurin Aokoka, 25: 53–59. (abstract).
Saxena, S., et al., 1985, Journal of Fermentation Technology 63: 307–310.
Ullrich, A., et al., 1984, The EMBO Journal, 3: 361–364.
Yamashita, T, et al., 1987 Molecular and General Genetics, 210: 462–467.

(List continued on next page.)

*Primary Examiner*—Ponnathapu Achutamurthy
*Assistant Examiner*—William W. Moore
*Attorney, Agent, or Firm*—Pennie & Edmonds LLP

[57] ABSTRACT

This invention relates to a novel DNA or a derivative thereof concerning the expression and secretion of a phenoloxidase gene originating in a basidiomycete (particularly a white rot fungus such as, for example *Coriolus hirsutus* IFO 4917) possessing the ability to produce and secrete a phenoloxidase, a novel organism containing the DNA and a protein-coding DNA, and a method for the production of proteins by the use of the novel organisms. The aforementioned "DNA concerning expression" generally refers as to a region existent on the upstream side of a structural gene and necessary for the initiation of transcription (promoter) and to a region existent on the downstream side thereof and necessary for the termination of the transcription (poly A signal or terminator), for example. The "DNA concerning secretion" generally refers to a DNA which codes a signal peptide. The aforementioned "DNA derivative" includes a still longer derivative accompanying a flanking sequence and variants associated with fragment of the DNA mentioned above, substitution of a nucleotide of the aforementioned DNA, insertion of a nucleotide, deletion of nucleotide, inversion of a nucleotide sequence, and other forms of mutation. These derivatives are obtained naturally, synthetically, or semisynthetically.

14 Claims, 8 Drawing Sheets

```
         10         20         30         40
GAATTCCCGA CACTGTTCGG GACGCGCGTC TTACCGCCGT
         50         60         70         80
GAGACGCAGG GCGTGTCGCG ACCTCTGCAA GCTCACACGC
         90        100        110        120
TTACCAGGGG ACTCGCGCGA TGGCCGCGTT CCAGGGCCGG
        130        140        150        160
CTTGACAGAT GCTGACACCG GTGCAATCTT GACACTGTGC
        170        180        190        200
CAACCGGGTA AGGCTCGTCC TTGGTTTGCT GGAGGCGCCC
        210        220        230        240
ACCGTTGAGC CTTGGCCATA CAGAGCGCTG TTCTTCGACG
        250        260        270        280
GGGTATAAAG GATGCCGCAG CGAACTCCCA ACAGCACAAC
        290        300        310        320
TCGAGCCCCG CTTGAGTTTC TACGAGGTCC TGCAAACCAC
        330        340        350        360
TGCCCCTCCT CCCGTCACAG CCATGTCGAG GTTCCAGTCT
        370        380        390        400
CTGCTCGCCT TCGTCGTCGC CTCTCTCGCG GCTGTGGCCC
        410
ATGCC
```

OTHER PUBLICATIONS

Hamer, J, et al., 1987, Molecular and Cellular Biology, 7:2352–2359.

Turgeon, B., et al., 1987, Molecular and Celluar Biology, 7: 3297–3305.

Wang, J., et al., 1988, Proc. Nat'l Acad. Sciences USA, 85: 865–869.

Hewick, R.M., et al., 1981, The Journal of Biological Chemistry, 256(15): 7990–7997.

Von Heijne, G., 1985, Journal of Molecular Biology 184:99–105.

Van Arsdell, J.N., et al., 1987, Bio/Technology 5(1):60–64.

FIG. 2

```
         10          20          30          40
GAATTCCCGA  CACTGTTCGG  GACGCGCGTC  TTACCGCCGT
         50          60          70          80
GAGACGCAGG  GCGTGTCGCG  ACCTCTGCAA  GCTCACACGC
         90         100         110         120
TTACCAGGGG  ACTCGCGCGA  TGGCCGCGTT  CCAGGGCCGG
        130         140         150         160
CTTGACAGAT  GCTGACACCG  GTGCAATCTT  GACACTGTGC
        170         180         190         200
CAACCGGGTA  AGGCTCGTCC  TTGGTTTGCT  GGAGGCGCCC
        210         220         230         240
ACCGTTGAGC  CTTGGCCATA  CAGAGCGCTG  TTCTTCGACG
        250         260         270         280
GGGTATAAAG  GATGCCGCAG  CGAACTCCCA  ACAGCACAAC
        290         300         310         320
TCGAGCCCCG  CTTGAGTTTC  TACGAGGTCC  TGCAAACCAC
        330         340         350         360
TGCCCCTCCT  CCCGTCACAG  CCATGTCGAG  GTTCCAGTCT
        370         380         390         400
CTGCTCGCCT  TCGTCGTCGC  CTCTCTCGCG  GCTGTGGCCC
        410
ATGCC
```

FIG. 3

```
         10         20         30         40
GAATTCCCGA CACTGTTCGG GACGCGCGTC TTACCGCCGT
         50         60         70         80
GAGACCGAGG GCGCTGTCAC CGACCTCTAC AAGCTCACAC
         90        100        110        120
GCTGACCAGG GGACTCGCGC GATGACCGCG TTCCAGGGCC
        130        140        150        160
GGCTTGACAG ATGCTGACAC CGGTGCAATC TTGACACTGT
        170        180        190        200
GCCAACCGGG TAAGGCGCGT CCTTGGTTTG CTGGAGGCGC
        210        220        230        240
CCACCGTTGA GCCTTGGCCA TACAGAGCGC TGTTCTTCGA
        250        260        270        280
CGGGGTATAA AGGATGCCGC AGCGAACTCC CAACAGCACA
        290        300        310        320
ACTTGAGCCC CGCTTGAGTT TCTACGAGGT CCTGCAAACC
        330        340        350        360
ACTGCCCTC CTCCCGTCAC AGCCATGTCG AGGTTCCAGT
        370        380        390        400
CTCTGCTCGC CTTCGTCGTC GCCTCCCTCG CGGCTGTGGC
        410
CCATGCC
```

FIG. 4

```
         10         20         30         40
TAGATGGCAC GTGGACCCTC GGCGGCACGG TATGGACAAT
         50         60         70         80
GACTTCGGAT TTACAACAAC GGACTTTCGT GGGAACTCCG
         90        100        110        120
AGTCGCTGGC CCGGTTGATG GGGCGGCCGA GGGAATTGGG
        130        140        150        160
CTTATCGTCG ACAGTACGAT TGTATAATTT GCTTAATGGT
        170        180        190        200
TCAAAACGGA AAGAATGCAA CACAGGGTTA TTATGGTCTT
        210        220        230        240
CGTTTGTCTG ACGTTCGGTG TTCCGTTTGC TGGATAGCGA
        250        260        270        280
TTGTGAATAA CTCTCGGGCT TTTCGAAGGG ACTGGCTTCA
        290        300        310        320
ATTCCACTTC AGCAAGGGTT TGAATGGAAC GAGAGCTATC
        330        340        350        360
TTACACTGTG CATATGCTTC ACGAACTCTT GTCCGCCGGC
        370        380        390        400
CACGTCGCAA TCTTCGTCGC GCGGCCCGTC AACGTGAACG
        410        420        430        440
TATGCTTGAG TGCGCCATCC GTGTCGAGCG CGAGCGTATA
        450
CGTCCCCGGG
```

FIG. 5

```
         10         20         30         40
TAGATGGAAC GTGGACCCTC GGCGGCACAG TATGGACAAT
         50         60         70         80
GACTTCGGAT TTACAACAAC GGACTTTCGT GGGAACTCCG
         90        100        110        120
AGTCGCTGGC CCGGTTGATG GGGCGGCCGA GGGAATTGGG
        130        140        150        160
TTATCGTCGA CAGTACGATT GTATAATTTG CTTAATGGTT
        170        180        190        200
CAAAACGGAA AGAATGCAAT ACAGGGTTAT TATGGTCATC
        210        220        230        240
ATCTGTATCA TGTCAGGTGG TCGATTGGCT GGTTGGCAAT
        250        260        270        280
CGTGAATGAC CCTCAGGCTT TTCGAAGGGA ATGACTGCGA
        290        300        310        320
CCTTACTATA ACAGGGCTTT GATTGGAGCG AGAGCTATCT
        330        340        350        360
TACACTGTAT ATGCACTTCA CGAACTCTTG TCCGCCGGCC
        370        380        390        400
ACGTCCCGAT CTTCGTCGCG GGGCCCGTCA ACGTGAACGT
        410        420        430        440
ATGCTTGAGT GCGCCATCCG TGTCGAGCGC GAGCGTATAC
        450
GTCCCCGGG
```

F I G. 6
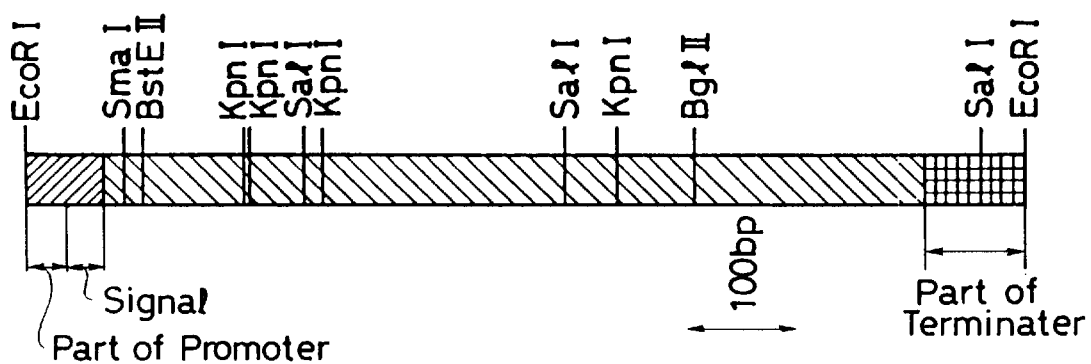

TRANSCRIPTIONAL REGULATORY DNA SEQUENCE ELEMENTS AND SIGNAL PEPTIDE SEQUENCE OF THE *CORIOLUS HIRSUTUS* PHENOLOXIDASE GENE, AND PLASMID VECTORS AND TRANSFORMANTS UTILIZING SUCH SEQUENCES

This is a File-Wrapper-Continuation of application Ser. No. 07/493,031, filed Mar. 13, 1990, now abandoned.

FIELD OF THE INVENTION

This invention relates to a novel DNA or a derivative thereof concerning the expression and secretion, a novel organism containing the DNA and a protein-coding DNA, and a method for the production of proteins by the use of the novel microorganism. More particularly, the present invention relates to a DNA or a derivative thereof concerning the expression and secretion of a phenol oxidase gene originating in a basidiomycete [particularly a white rot fungus such as, for example *Coriolus hirsutus* IFO 4917] possessing the ability to produce and secrete a phenoloxidase, a novel organism containing the DNA and a protein-coding DNA, and a method for the production of proteins by the use of the novel organisms.

The term "DNA concerning expression" generally refers as to a region existent on the upstream side of a structural gene and necessary for the initiation of transcription (promoter) and to a region existent on the downstream side thereof and necessary for the termination of the transcription (poly A signal or terminator), for example. The term "DNA concerning secretion" generally refers to a DNA which codes a signal peptide.

The "DNA derivative" includes a still longer derivative accompanying a flanking sequence as well as variants comprising a fragment of the DNA mentioned above, variants with a substituted nucleotide of the DNA mentioned above, variants with an inserted nucleotide, variants with a deleted nucleotide, variants with an inverted nucleotide sequence and variants with other forms of mutation. These derivatives are obtained naturally, synthetically, or semisynthetically.

BACKGROUND OF THE INVENTION

To date, numerous efforts have been made to fulfil the purpose of realizing quantity production of a useful protein by the use of the technique of gene recombination.

The technique of gene recombination for the quantity production of a useful protein basically comprises a host, a vector, and a gene coding a useful protein.

The hosts which are usable for this technique include procaryotes such as *Escherichia coli* and *Bacillus subtilis* and eucaryotes such as yeast, animal cell, and plant cell. In the selection of a host for a particular recombination, due consideration is paid to the characterization of a protein subjected to expression and the use for which the produced protein is intended.

As regards the vector to be used for the recombination, a large number of widely varying vectors have been developed to date. There are four basic functions which are required of a vector; (1) an ability to form an in vitro recombinant with a DNA which codes the protein aimed at, (2) an ability to attain growth in the cell of the host aimed at, (3) an ability to attain introduction in the cell of the host aimed at, and (4) ability to effect specific detection of a cell possessing a recombinant DNA. For the purpose of fulfilling quantity production of the useful protein, the vector is further required to possess these additional functions; (5) ability to possess a strong promoter and a terminator (DNA sequences concerning expression) and (6) an ability to possess a signal sequence (DNA sequences concerning secretion), for example.

A strong promoter is necessary for and indispensable to quantity production of a protein. The secretion of a mass-produced protein by a signal sequence is effective in preventing intracellular accumulation of a protein harmful to the host, precluding decomposition of a product by a protease in the cell, and simplifying and economizing the process of purification of a useful protein which has heretofore entailed expenditure of great labor and cost.

Owing to the advantages mentioned above, efforts are being continued in research and development of strong promoters and signal sequences excelling in efficiency of secretion.

In the case of *Escherichia coli* as a procaryote, a $P_L O_L$ promoter for λ phage, a lac promoter for lactose operon, a trp promoter for tryptophan operon, a lpp promoter and a signal sequence for an outer-membrane protein gene, and a lacUV5 promoter and a tac promoter as improved versions thereof have been developed. In the case of *Bacillus subtilis*, a penP for an enzyme penicillinase gene outside bacteria and a promoter and a signal sequence for an α-amylase have been developed.

In the case of yeasts as an eucaryote, promoters for a group of glycolytic enzymes have been demonstrated as effective for strong and over expression of proteins. For example, promoters and a-factors and signal sequence of such α-factor for genes such as 3-phosphoglycerate kinase (PGK), glyceraldehyde triphosphoric acid dehydrogenase (GLD), enolase (ENO), triose phosphoric acid isomerase (TPI), alcohol dehydrogenase (ADH), acidic phosphatase (PHO), and the galactose metabolic system (GAL), have been developed and put to use.

The number of cases of successful development of promoters usable for cells of higher animals is still small. Though promoters for early gene and late gene of the virus SV40 attaining satisfactory propagation in the cell of monkey, a promoter for an ICP gene of HSV, a promoter for an early gene of vaccinia virus, a promoter for a chicken β-actin, a promoter for a human EF-1a gene, and an IgG H chain promoter have been developed, they are not fit for the purpose of quantity production of useful proteins.

As regards promoters which are usable for the technique of gene recombination using a plant as a host, a promoter for the 35S gene of a cauliflower mosaic virus, a promoter for a nopalin synthetic gene of a Ti plasmid, and an ORF12 promoter for a Ri plasmid have been developed. Again, these promoters are unfit for the purpose of over-production of useful proteins.

Recently, development of systems for secretionary production of useful proteins by the use of a mold particularly of genus Aspergillus has come to appear in literature. The secretionary production of such proteins as lipase and prochymosin by the use of a promoter for a glucoamylase gene of *Aspergillus niger* and a signal sequence has been realized, for example.

This statement does not necessarily mean that the use of systems capable of expression and secretion of mold of genus Aspergillus permits efficient and secretionary over production of all useful proteins. Thus, efforts are being continued in research and development of a system capable of more efficient expression and secretion.

Incidentally, a technique of gene recombination using a basidiomycete as a host remains yet to be established. The basidiomycetes include numerous useful fungi such as edible mushroom, fungi producing physiologically active substances, fungi capable of decomposing lignin and useful for biological pulping and biobleaching, and fungi decomposing cellulose and saccharifying lignous components. Attempts at improving and fortifying the characteristics of these fungi and breeding these fungi have been made heretofore with a method resorting to mating, a method resorting to acquisition of a variant, and a method resorting to cell fusion, for example. If a method for molecular breeding by the use of the technique of gene recombination is realized, it would allow easy acquisition of excellent strains.

Further, since the safety of using basidiomycetes for food, similar to that of *Aspergilus oryzae* (Koji-mould), has been already established, these basidiomycetes are highly useful as hosts for the production of proteins. An attempted use of a filamentous plasmid DNA occurring in the mitochondria of *Lentinus edodes* (Shiitake) and *Pleurotus ostreatus* (Hiratake) as a vector for a basidiomycete has been reported ("Iden [genetics]," vol. 42, No. 9, p. 20, Shokabo, 1988). It has been shown, however, that the filamentous plasmid DNA has problems such as lack of stability within the host and has not been perfected for practical use so far.

No promoter has been so far developed which is used effectively for basidiomycetes. Virtually no successful cloning of a gene for providing a promoter has yet been reported in literature, except for a report concerning a ligninase gene obtained by cloning with a microorganism of genus *Phanerochaete chrysosporium*. This gene is characterized by expressing ligninase by virtue of secondary metabolism and the extent of this expression is not appreciably large. Thus, the gene does not deserve to be called an effective promoter. In the circumstances, a desire has been expressed in the industry to develop a promoter and a signal sequence which are capable of effecting efficient secretion and expression of useful proteins with basidiomycete. The promoter and signal sequence thus yearned for are required to effect strong expression in a wide variety of hosts and possess a signal sequence for allowing secretion of a protein produced by the expression.

The Phenoloxidase which is a useful protein is such that the gene thereof, when introduced in a varying organism and expressed therein, can be utilized for biological pulping, biobleaching, decolorization of plant effluent, and pretreatment of wood in saccharification and can be used otherwise as a reagent for clinical tests.

The gene which codes this phenoloxidase has been developed and identified by the present inventors in accordance with a technique of cloning *Coriolus hirsutus* IFO 4917, i.e. a white-rot fungus [Japanese Patent Application 88-175,235 and 88-175,236].

A promoter and a signal sequence which are available for effecting expression, particularly secretionary expression, of this phenoloxidase gene, however, remain yet to be developed.

[Problem for Solution by the Invention]

The present inventors have pursued a diligent study with a view to fulfilling the demand for development of a promoter, a signal sequence, and a terminator capable of secretionary production of all useful proteins in large amounts, particularly the demand for development of such substances usable even with basidiomycetes. They have consequently succeeded in developing novel DNA's, i.e. a promoter, a signal sequence, and a terminator, concerning the expression and secretion, which attain secretionary production of phenoloxidase in a basidiomycete in a large amount.

SUMMARY OF THE INVENTION

To be specific, this invention comprises the following elements (1) to (12).

(1) A DNA (I) or a derivative thereof, coding a region concerning the expression and secretion of a protein containing the following sequences or a derivative of the region.

| | 10 | 20 | 30 | 40 |
|---|---|---|---|---|
| | GAATTCCCGA | CACTGTTCGG | GACGCGCGTC | TTACCGCCGT |
| | 50 | 60 | 70 | 80 |
| | GAGACGCAGG | GCGTGTCGCG | ACCTCTGCAA | GCTCACACGC |
| | 90 | 100 | 110 | 120 |
| | TTACCAGGGG | ACTCGCGCGA | TGGCCGCGTT | CCAGGGCCGG |
| | 130 | 140 | 150 | 160 |
| | CTTGACAGAT | GCTGACACCG | GTGCAATCTT | GACACTGTGC |
| | 170 | 180 | 190 | 200 |
| | CAACCGGGTA | AGGCTCGTCC | TTGGTTTGCT | GGAGGCGCCC |
| | 210 | 220 | 230 | 240 |
| | ACCGTTGAGC | CTTGGCCATA | CAGAGCGCTG | TTCTTCGACG |
| | 250 | 260 | 270 | 280 |
| | GGGTATAAAG | GATGCCGCAG | CGAACTCCCA | ACAGCACAAC |
| | 290 | 300 | 310 | 320 |
| | TCGAGCCCCG | CTTGAGTTTC | TACGAGGTCC | TGCAAACCAC |
| | 330 | 340 | 350 | 360 |
| | TGCCCCTCCT | CCCGTCACAG | CCATGTCGAG | GTTCCAGTCT |
| | 370 | 380 | 390 | 400 |
| | CTGCTCGCCT | TCGTCGTCGC | CTCTCTCGCG | GCTGTGGCCC |
| | ATGCC | | | |

(2) A DNA (II) or a derivative thereof, coding a region concerning the expression and secretion of a protein containing the following sequences or a derivative of the region.

| | 10 | 20 | 30 | 40 |
|---|---|---|---|---|
| | GAATTCCCGA | CACTGTTCGG | GACGCGCGTC | TTACCGCCGT |
| | 50 | 60 | 70 | 80 |
| | GAGACCGAGG | GCGCTGTCAC | CGACCTCTAC | AAGCTCACAC |
| | 90 | 100 | 110 | 120 |
| | GCTGACCAGG | GGACTCGCGC | GATGACCGCG | TTCCAGGGCC |
| | 130 | 140 | 150 | 160 |
| | GGCTTGACAG | ATGCTGACAC | CGGTGCAATC | TTGACACTGT |
| | 170 | 180 | 190 | 200 |
| | GCCAACCGGG | TAAGGCGCGT | CCTTGGTTTG | CTGGAGGCGC |
| | 210 | 220 | 230 | 240 |
| | CCACCGTTGA | GCCTTGGCCA | TACAGAGCGC | TGTTCTTCGA |
| | 250 | 260 | 270 | 280 |
| | CGGGGTATAA | AGGATGCCGC | AGCGAACTCC | CAACAGCACA |
| | 290 | 300 | 310 | 320 |
| | ACTTGAGCCC | CGCTTGAGTT | TCTACGAGGT | CCTGCAAACC |
| | 330 | 340 | 350 | 360 |
| | ACTGCCCCTC | CTCCCGTCAC | AGCCATGTCG | AGGTTCCAGT |

-continued

```
       370         380         390         400
  CTCTGCTCGC  CTTCGTCGTC  GCCTCCCTCG  CGGCTGTGGC

CCATGCC
```

(3) A DNA (III) or a derivative thereof, coding a region concerning the expression of a protein containing the following sequence.

```
        10          20          30          40
  TAGATGGCAC  GTGGACCCTC  GGCGGCACGG  TATGGACAAT 50          60          70          80
  GACTTCGGAT  TTACAACAAC  GGACTTTCGT  GGGAACTCCG 90         100         110         120
  AGTCGCTGGC  CCGGTTGATG  GGGCGGCCGA  GGGAATTGGG 130         140         150         160
  CTTATCGTCG  ACAGTACGAT  TGTATAATTT  GCTTAATGGT 170         180         190         200
  TCAAAACGGA  AAGAATGCAA  CACAGGGTTA  TTATGGTCTT 210         220         230         240
  CGTTTGTCTG  ACGTTCGGTG  TTCCGTTTGC  TGGATAGCGA 250         260         270         280
  TTGTGAATAA  CTCTCGGGCT  TTTCGAAGGG  ACTGGCTTCA 290         300         310         320
  ATTCCACTTC  AGCAAGGGTT  TGAATGGAAC  GAGAGCTATC 330         340         350         360
  TTACACTGTG  CATATGCTTC  ACGAACTCTT  GTCCGCCGGC 370         380         390         400
  CACGTCGCAA  TCTTCGTCGC  GCGGCCCGTC  AACGTGAACG 410         420         430         440
  TATGCTTGAG  TGCGCCATCC  GTGTCGAGCG  CGAGCGTATA

450
  CGTCCCCGGG
```

(4) A DNA (IV) or a derivative thereof, coding a region concerning the expression of a protein containing the following sequence.

```
        10          20          30          40
  TAGATGGAAC  GTGGACCCTC  GGCGGCACAG  TATGGACAAT 50          60          70          80
  GACTTCGGAT  TTACAACAAC  GGACTTTCGT  GGGAACTCCG 90         100         110         120
  AGTCGCTGGC  CCGGTTGATG  GGGCGGCCGA  GGGAATTGGG 130         140         150         160
  TTATCGTCGA  CAGTACGATT  GTATAATTTG  CTTAATGGTT 170         180         190         200
  CAAAACGGAA  AGAATGCAAT  ACAGGGTTAT  TATGGTCATC 210         220         230         240
  ATCTGTATCA  TGTCAGGTGG  TCGATTGGCT  GGTTGGCAAT 250         260         270         280
  CGTGAATGAC  CCTCAGGCTT  TTCGAAGGGA  ATGACTGCGA 290         300         310         320
  CCTTACTATA  ACAGGGCTTT  GATTGGAGCG  AGAGCTATCT 330         340         350         360
  TACACTGTAT  ATGCACTTCA  CGAACTCTTG  TCCGCCGGCC
```

-continued

```
       370         380         390         400
  ACGTCCCGAT  CTTCGTCGCG  GGGCCCGTCA  ACGTGAACGT 410         420         430         440
  ATGCTTGAGT  GCGCCATCCG  TGTCGAGCGC  GAGCGTATAC

450
  GTCCCCGGG
```

(5) A DNA or a derivative thereof according to any of (1) to (4), wherein the protein is a phenoloxidase.

(6) A DNA molecule or a derivative thereof, coding a peptide concerning the secretion of a protein comprising the following amino acid sequence.

```
  Met Ser Arg Phe Gln Ser Leu Leu Ala Phe

Val Val Ala Ser Leu Ala Ala Val Ala His

Ala
```

(7) A DNA molecule or a derivative thereof, coding a region concerning the secretion of a protein comprising the following sequence.

```
  ATGTCGAGGTTCCAGTCTCTGCTCGCCTTCGTCGTCGCCTCT

CTCGCGGCTGTGGCCCATGCC
```

(8) A DNA or a derivative thereof according to (6) or (7), wherein the protein is a phenoloxidase.

(9) A novel organism expressing and secreting a protein containing a protein-coding DNA and a DNA or a derivative thereof set forth in any of (1) to (7).

(10) A novel organism according to (9), wherein the protein is a phenoloxidase.

(11) A method for the production of a protein, characterized by effecting transformation of a cell a by protein-coding DNA and a DNA or a derivative thereof concerning the expression of the protein-coding DNA, culturing said cell, and obtaining proteins from the resultant culture broth.

(12) A method according to (11), wherein the protein is a phenoloxidase.

BRIEF DESCRIPTION OF THE DRAWINGS

FIG. 2 is a DNA (I) concerning expression and secretion of the phenoloxidase gene originating in the chromosome.

FIG. 3 is a DNA (II) concerning expression and secretion of the phenoloxidase gene originating in the chromosome.

FIG. 4 is a DNA (III) terminator concerning expression of the phenoloxidase gene originating in the chromosome.

FIG. 5 is a DNA (IV) terminator concerning expression of the phenoloxidase gene originating in the chromosome.

FIG. 6 is a restriction endonuclease physical map of the phenoloxidase gene originating in the mRNA and the DNA concerning secretion.

DETAILED DESCRIPTION OF THE INVENTION

Figure 1:
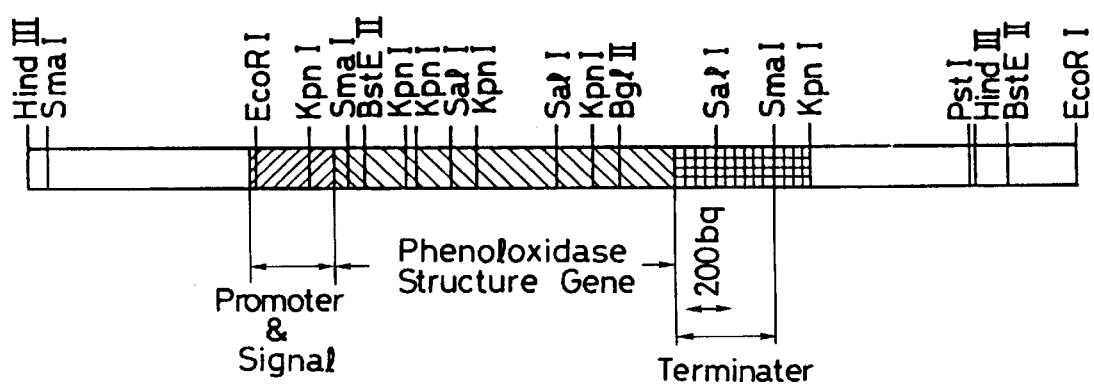
FIG. 1 is a restriction endonuclease physical map of the structural gene of the phenoloxidase gene originating in the chromosome and the DNA concerning expression and secretion.

The present inventors have studied phenoloxidases and DNA sequences for expression and secretion of phenoloxidases such as promoters capable of effecting quantity expression of useful proteins and signal sequence capable of effecting efficient secretion of produced enzymes, to find that the promoters and signal sequences of phenoloxidases produced by various organisms (particularly basidiomycetes) are effective.

They have found that particularly basidiomycetes of the group including *Coriolus hirsutus* IFO 4917 are suitable sources for DNA's as evidenced by the fact that they allow quantity secretionary production of phenoloxidases constitutively on being subjected to liquid culture. They have succeeded in isolating DNA's concerning expression and secretion of such basidiomycetes as mentioned above.

The DNA's concerning expression are obtained solely on the chromosomes such as of basidiomycetes and the DNA's concerning secretion can be obtained from both chromosomes and mRNA's of basidiomycetes.

The DNA's concerning expression and secretion, similarly to those disclosed in Japanese Patent Application 88-175,235 or Japanese Patent Application 88-175,136, can be isolated from the chromosome DNA library or the cDNA library, with a synthetic DNA probe or with the structural gene of a cloned phenoloxidase as a probe.

The isolated DNA concerning expression and secretion is allowed to effect secretionary production of phenoloxidase by being linked with the structural gene of phenoloxidase, then linked with a suitable vector, and introduced into a host cell as ordinarily practised by the gene recombination technique.

The aforementioned DNA's concerning expression and secretion, as described above, promote the expression and secretion of phenoloxidase genes. The DNA sequences, however, are effective in the expression and secretion of proteins other than the proteins mentioned above. The DNA sequences which code the amino acid sequences mentioned above are effective not only in secreting phenoloxidase but also in secreting other proteins.

Now, the present invention will be described in detail below.

(Preparation of DNA probe)

The DNA probe which is required for selecting the DNA molecule concerning the expression and secretion of a phenoloxidase from the chromosomal DNA library composed of chromosomes and the cDNA library composed of mRNA's may be similar to the synthetic DNA probe which the present inventors used in cloning the phenoloxidase gene (Japanese Patent Application 88-175,235 and Japanese Patent Application 88-175,236). It is otherwise permissible to use a cloned phenoloxidase structural gene or a DNA molecule synthesized based on a structural gene as the probe.

Specifically, the sequence of the synthetic DNA probe is determined on the basis of the partial amino acid sequence of phenoloxidase. And the partial amino acid sequence of phenoloxidase is determined by subjecting the amino acid sequence from the N-terminal of phenoloxidase produced and purified by the method disclosed in Japanese Patent Laid open 86-285,989, Japanese Patent Laid open 87-220,189, Japanese Patent Laid open 87-220,190 and purified phenoloxidase to CNBr degradation [Co.o., R.D.: Methods Enzymol. 11, 315–317 (1967) or trypsin degradation [Lin, L.-N. & Brandts. J. F.: Biochemistry 22, 553 (1983)], and subjecting the amino acid sequence from the N-terminal of the separated polypeptide to the Edman degradation method [Edman, P & Henshchen, A. Protein Sequence determination, 2nd ed., Springer-Verlag. Berlin, pp 232–279 (1975)].

The synthesis of the DNA probe can be performed by any of the phosphodiester method, phosphotriester method, phosphite method, and amidite method which is an improved version thereof.

It is further permissible to use as a DNA probe the structural gene of the phenoloxidase possessed by the strains cloned by the present inventors and deposited with Fermentation Research Institute, Agency of Industrial Science and Technology under FERM BP-2793, FERM P-10055, and FERM P-10061. The DNA probe synthesized on the basis of the sequence of the phenoloxidase structural gene disclosed by the present inventors in Japanese Patent Application 88-175,235 and Japanese Patent Application 88-175,236 is also usable.

(Preparation of chromosome DNA)

The phenoloxidase-originating organism which is usable in the present invention may be any of the organisms which possess phenoloxidase at all. Among other phenoloxidase-originating organisms, white-rot fungi [such as, for example, *Coriolus hirsutus* (IFO 4917), *Coriolus versicolor* (IFO 30340), and *Lenzites edodes* (IFO 8714)] which produce and secrete phenoloxidases of particularly high enzymatic activity prove to be desirable.

As regards the composition of the culture medium to be used for the growth and propagation of a white-rot fungus, while glucose is used as a main carbon source, other carbon sources which can be assimilated by the white-rot fungus may be used. While yeast extract and polypeptone are used as main nitrogen sources, inorganic nitrogen compounds such as ammonium salts and nitrates and organic nitrogen-containing substances such as urea and casein which can be assimilated by the white-rot fungus may be used. Optionally, the culture medium may additionally incorporate therein such inorganic salts as calcium salts, magnesium salts, potassium salts, phosphates, manganese salts, zinc salts, and iron salts and such nutritional substances as corn steep liquor, vitamins, amino acids, and nucleic acids and growth-promoting substances.

A white-rot fungus is inoculated to the aforementioned culture medium and cultured therein. After the culture, the cells are collected, frozen in liquefied nitrogen, ground in a mortar, and extracted by the phenol extraction method to separate the chromosomal DNA. The separated chromosomal DNA is purified to obtain a chromosomal DNA used for construction of a chromosomal DNA library.

The extraction of the chromosomal DNA can be attained efficiently by subjecting the ground mass of cell bodies to a treatment with a proteinase before it is subjected to the phenol extraction of chromosomal DNA.

(Construction of chromosomal DNA library)

The vector to be used for the chromosomal DNA library may be any of the vectors conventionally used for the purpose. In the case of a eucaryote which has a large volume of chromosomal DNA, it is believed proper to use a cosmid vector which is selected from a small number of vectors. The method of this invention will be described hereinbelow on the assumption that a cosmid vector is used as the vector.

A chromosomal DNA cosmid library is constructed with a cosmid vector pHC79 [Hohn, B. and Collins, J. (1980)

Gene 11, 291] as a vector. The cosmid vector pHC79 is available in the form of commercial products (such as, for example, the product of Bethesda Research Laboratories marketed under product code of 5358SA and the product of Boehringer Mannheim-Yamanouchi K.K. and marketed under product code of "567795"].

Chromosomal DNA fragments of sizes in the range of 32 to 46 Kb (kilo-base pairs) are obtained by partially digesting the aforementioned chromosomal DNA with a restriction endonuclease Sau 3AI (produced by Takara Shuzo Co., Ltd. and marketed under product code of "1082A"). Separately, the cosmid vector pHC79 is completely digested with a restriction endonuclease BamHI (produced by Takara Shuzo Co., Ltd. and marketed under product code of "1010"), treated for removal of phosphoric acid, combined with the partially digested fragments of chromosomal DNA mentioned above, and subjected to a reaction with a T4 DNA ligase (produced by Takara Shuzo Co., Ltd. and marketed under product code of "2011A") for ligation of DNA chain.

The product of this ligation consequently obtained is inserted in mature phage particle with the aid of a commercially available in vitro packaging kit [such as, for example, the product of Amersham Japan Ltd. and marketed under product code of "N. 334Y" and the product of Promega Corporation and marketed under product code of "P3151"], infected with an $E.$ $coli$ strain DH 1 (ATCC 33849) to obtain about 50,000 clones of Apr (Ampicillin-resistant) per 1 $\mu$g of chromosomal DNA. The clones are used as the cosmid library of chromosomal DNA.

(Cloning of DNA molecule concerning expression and secretion of phenoloxidase gene)

About 10,000 of recombinants of $E.$ $coli$ in cosmid library are cultured on a LB culture medium containing Ampicillin (containing 10 g of Bactotrypton, 5 g of Bacto yeast extract, 10 g of sodium chloride, and 15 g of agar each per liter) to form colonies therein.

The colonies are replicated on a commercially available nitrocellulose or nylon filter [such as, for example, the product of Amersham Japan K.K. marketed under product code of "RPN. 82C" and the product of Toyo Roshi K.K. marketed under product code of "A045B082C"], to immobilize the DNA on the filter by the conventional method [Grunstein, M. & D. S. Hogness: Proc. Natl. Acad. Sci. USA 72, 3961 (1975)].

The DNA on the filter and the synthetic DNA probe labelled with a radioisotope $^{32}$p [Produced by Amersham Japan K.K. and marketed under product code of "PB10168"] by the method disclosed in Richardson, C. C. (1965) Proc. Natl. Acad. Sci. U.S.A. 54, 158 to 161 or the phenoloxidase structural gene labelled by the nick translation method [Berg. P. (1977) J. Mol. Biol. 113, 237 to 251] or the random hexamer DNA labelling method [Feinberg, A. P. and Voegelstein B. (1983), Anal. Biochem. 132, 6 to 13] are hybridized to select the $E.$ $coli$ incorporating therein a DNA concerning expression and secretion of the phenoloxidase structural gene. The cosmid is extracted from the selected $E.$ $coli$ by the conventional method and is purified.

In the chromosomal DNA segment incorporated in the cosmid, the part containing the DNA concerning the expression and secretion of the phenoloxidase gene is restricted, sectioned for sub-cloning with a restriction endonuclease HindIII [produced by Takara Shuzo Co., Ltd. and marketed under product code of "1060S"], EcoRI [produced by Takara Shuzo Co., Ltd. and marketed under product code of "1040S"] or SmaI [produced by Takara Shuzo Co., Ltd. and marketed under product code of "1085A"] and separated by molecular weight by the agarose gel electrophoretic method.

The chromosomal DNA fragment immobilized on the filter and the DNA probe labelled with $^{32}$p are hybridized. The DNA fragment hybridized with the DNA probe is sub-cloned into the plasmid vector pUC19 [Yanisch-Perron, C. Vieira, J. and Messing, J (1985) Gene, 33, 103, Messing, J. (1983) Method in Enzymology, 101, 20–78, produced by Takara Shuzo Co. Ltd. and marketed under product code of "3219"] to produce a restriction endonuclease physical map.

The incorporation into the vector DNA of the consequently obtained DNA fragment containing the DNA concerning expression and secretion of the phenoloxidase gene is carried out as follows. Vector DNA fragments are prepared by cutting the vector DNA by the use of a suitable restriction endonuclease. Then, the mixture of the DNA fragment containing the DNA concerning the expression and secretion of the phenoloxidase gene with the vector DNA fragment is treated with a T4 DNA ligase. The vector DNA's which are usable herein include pBR322, pUC18, and pUC19 [produced by Takara Shuzo Co., Ltd. and marketed under product codes of "3050, 3218, 3219," etc.], for example. The restriction endonucleases which are usable herein include HindIII, EcoRI, and PstI [produced by Takara Shuzo Co., Ltd. and marketed under product code of "1073S"], and BamHI, for example.

The recombinant DNA having the DNA concerning the expression and secretion of phenoloxidase gene ligated with the vector DNA is obtained as described above.

(Determination of base sequence of DNA concerning expression and secretion of phenoloxidase gene)

The DNA fragment sub-cloned to the plasmid vector pUC19 is in principle treated by the Henikoff's method and the Yanisch-Perron's method [Henikoff, S. (1984), Gene, 28, 351 to 359, Yanisch-Perron, C., Vieira, J. and Messing, J. (1985) Gene, 33, 103–119] to produce deletion mutants. Optionally, a commercially available deletion kit [the product of Takara Shuzo Co., Ltd. and marketed under product code of "6030"] may be used instead.

The deletion mutants are tested by the dideoxy method [Sanger, F. (1981) Science, 214, 1205–1210] for base sequencing. Optionally, a commercially available sequencing kit [such as, for example, the product of Takara Shuzo Co., Ltd. marketed under product codes of "6010A, 6015A") and the product of Nippon Gene K.K. marketed under product code of "317-01121"] instead.

(Preparation of mRNA)

The phenoloxidase-originating organism which can be used for the preparation of mRNA, similarly to what is used for the preparation of the chromosomal DNA, may be any of the organisms which possess a phenoloxidase at all. White-rot fungi [such as, for example, $Coriolus$ $hirsutus$ IFO 4917, $Coriolus$ $versicolar$ IFO 30340, and $Lenzites$ $betulins$ IFO 8714] which produce and secrete a particularly high active enzyme are used advantageously.

Such a white-rot fungus is cultured in the same manner as in the preparation of the chromosomal DNA. When the phenoloxidase activity in the culture broth reaches its maximum, the cells are collected and frozen in a liquefied nitrogen.

The extraction of the total mRNA corresponding to such proteins as phenoloxidase from the white-rot fungus may be carried out by the conventional method. For example, the extraction can be effected by a procedure which comprises mixing the cell bodies of white-rot fungus with 2 to 5 times as large in volume of such a surfactant as NP-40, SDS, or Triton X-100 and a phenol solution, subjecting the resultant mixture of such a physical treatment as homogenization or freeze melting thereby comminuting and solubilizing the cell bodies, centrifuging the resultant mixture, separating the supernatant from the centrifuged layers, and adding cold ethanol to the separated supernatant thereby inducing precipitation of RNA. Alternatively, the extraction may be accomplished by the GTC method which comprises crushing a tissue in a guanidine thiocyanate solution, causing precipitation of ethanol in the resultant solution, and repeating solution of the precipitate with guanidine hydrochloride thereby effecting extraction of total mRNA. Broda et al's method [J. Microbiol. Methods, 4, (1985) 155–162] may be employed instead. Otherwise, the extraction of the total mRNA may be attained by the use of a commercially available RNA extraction kit [produced by Amersham Japan K.K. and marketed under product code of "RPN. 1264"]. Optionally, the method which comprises causing precipitation of a polysome in process of phenoloxidase synthesis with an antibody corresponding to the phenoloxidase and extracting the mRNA from the precipitated polysome as with a surfactant may be employed.

The poly(A)mRNA of this invention may be purified by the method resorting to the use of an adsorption column packed with oligo(dT) cellulose or poly(U)cellulose or by the method of the fractionation of resorting to the sucrose density gradient centrifugation, for example.

The presence of the mRNA corresponding to the phenoloxidase aimed at in the total mRNA obtained as described above may be attained as by the method which comprises translating the mRNA into a protein and identifying this protein by the use of a corresponding antibody. Specifically, it is possible to translate the mRNA into the protein with an acellular medium such as, for example, Reticulocyte lysate or Wheat germ which is frequently used in the translation of mRNA into a protein and confirm that the mRNA corresponding to the phenoloxidase possesses activity.

This confirmation may be otherwise attained by the dot hybridization using a DNA probe of phenoloxidase or by the northern blot hybridization.

The mRNA obtained as described above is used for in vitro synthesis of a cDNA. The cDNA is incorporated in a suitable vector and used for the construction of a cDNA library for cloning the DNA concerning secretion of a phenoloxidase gene.

(Synthesis of cDNA)

The methods which are available for the synthesis of cDNA include the Gubler-Hoffman method, the Rand Method, the Okayama-Berg method, and the modified versions thereof, for example. The synthesis may be carried out, for example, in vitro by the following method. With the aforementioned mRNA as a template and an oligo(dT) as a primer, a single-chain cDNA complementary to the mRNA is synthesized with a reverse transcriptase [produced by Takara Shuzo Co., Ltd. and marketed under product code of "2610A"] in the presence of dNTP (=dATP, dGTP, dCTP, dTTP). Then, a double-chain cDNA is synthesized by inserting a cut in the mRNA with a RNaseH (produced by Takara Shuzo Co., Ltd. and marketed under product code of "2150A") and causing a DNA polymerase I (produced by Takara Shuzo Co., Ltd. and marketed under product code of "2140A") to react upon the mRNA as a primer in the presence of dNTP. This method of synthesis is obtained by the use of a commercially available cDNA synthesizing kit [such as the product of Amersham Japan K.K. under product code of "RPN. 1256Y") and the product of Boehringer Mannheim-Yama nouchi K.K. and marketed under product code of "1013882"].

(Construction of cDNA library)

The double-chain cDNA mentioned above is allowed to construct a cDNA library by linking synthetic linkers one each to the opposite terminals thereof or by adding suitable tails (such as, for example, poly C's) thereto through the medium of a terminal transferase (produced by Takara Shuzo Co., Ltd. and marketed under product code of "2230A") and ligating the cDNA to a plasmid vector or a λ phage vector.

This construction of the cDNA library may be accomplished, for example, by linking an EcoRI Linker to the double-chain cDNA with a DNA ligase originating in T4 phage, then cutting the double-chain cDNA with a restriction endonuclease (produced by Takara Shuzo Co., Ltd. and marketed under product code of "1040S") thereby obtaining a double-chain cDNA possessing an EcoRI adhesive terminal, incorporating the double-chain cDNA at the EcoRI site in the phage vector λgt11, and subjecting the product of this incorporation to the in vitro packaging (with the package produced by Amersham Japan K.K. and marketed under product code of "N.334Y" or produced by Promega Corporation and marketed under product code of "P3151").

It is also permissible to use a commercially available cDNA library kit of λgt11 or λgt10 [such as, for example, the product of Amersham Japan K.K. marketed under product code of "RPN. 1280 or RPN. 1257" or the product of Promega Corporation marketed under product code of "P3010") for the construction under discussion.

(Cloning of DNA concerning secretion of phenoloxidase gene)

The cDNA containing the DNA concerning the secretion of the phenoloxidase gene originating in the mRNA is cloned by the plaque hybridization or colony hybridization using the DNA probe of phenoloxidase labelled with a radioisotope.

The consequently obtained DNA concerning the secretion of the mRNA phenoloxidase gene can be sequenced by being sub-cloned to a suitable vector in the same manner as in the DNA concerning the expression and secretion of the phenoloxidase gene originating in the chromosome DNA.

(Secretionary production of protein)

The utility of the DNA molecule concerning the expression and secretion of the phenoloxidase structural gene obtained as described above resides in efficiently producing and secreting a protein by connecting the DNA molecule to the structural gene of protein by the conventional method, incorporating the product of this connection in a suitable vector, and introducing the production of incorporation in the microorganism, animal cell and plant cell, as the host of the vector. The introduction into the host organism can be attained, for example, by the method which comprises effecting connection to the vector of plasmid, cosmid, phage, or virus and forming a recombinant by transformation or transduction or by the method which comprises forming the recombinant by directly introducing a DNA molecule as by electroporation.

Various hosts can be used herein. Among other hosts, *Escherichia coli* and other microorganisms belonging to genus Escherichia, *Bacillus subtilis* and other microorganisms belonging to genus Bacillus, *Saccharomyces cerevisiae* and other yeasts of genus Saccharomyces, the cells of tobacco and petunia and other plants of Family Solanaceae, and cultured animal cells such as BalbIC 3T3 prove to be particularly desirable.

The vectors which are used for these hosts are cited below.

EK type (stringent type) plasmid vectors such as pSC101, pRK353, pRK646, pRK248, and pDF41; EK type (relaxed type) plasmid vectors such as CalE1, pVH51, pAC105, RsF2124, pCR1, pMB9, BR313, pBR322, pBR324, pBR325, pBR327, pBR328, pKY2289, pKY2700, pKN80, pKC7, pKB158, pMX2004, pACYC1, pACYC184, and λdul; λgt type phage vectors such as λgt·λC, λgt·λB, λWES·λB, λZJvir·λB, λALO λB, λWES·Ts622, λDam, and λgt11; Charon vectors such as Charon 4A, Charon 3A, Charon 16A, Charon 13A, Charon 14A, Charon 15, Charon 8, Charon 10, Charon 17, and Charon 20; Tiolais group vectors such as L512, λZEQS, λZYV5φ, λZUVφ2, λZUVφ3, λYEQSφ1, λYEQSφ, λYEQSφ3, λBam, and λS51; plasmid vectors of *Bacillus subtilis* such as pTA1015, pLS15, pTA1020, pLS28, pLS13, pTA1050, pTA1060, pTA1030, and pTA1031; plasmid vectors originating in Staphylococcus such as pT127, pC194, pC221, pC223, pUB112, pUB110, pSA0501, pSA0501, pSA2100, pE194, pTP4, and pTP5; yeast vectors such as pJDB219, YEp13, YRp7, YIp1, pYC, and pTC2; plant vectors including various vectors originating in Ti plasmid and various vectors (including binary vectors) originating in *Cauliflower mosaic virus*; and animal vectors originating in $SV_{40}$ such as $pSVK^+$, pI-11β-, $pAVH_{in}$+K+, pβ2X, and pSXβ+. In the case of a plant vector originating in Ti plasmid, the produced recombinant DNA can be introduced in the host plant by introducing the recombinant DNA provisionally as in *Agrobacterium tumefaciens* T37 and infecting the plant cell with the recombinant microorganism as by co-culture.

In the case of a system using as its host an organism for which neither a host nor a vector has yet been developed, i.e. molds of genus Aspergillus and the genus Neurospora and basidiomycetes including *Coriolus hirsutus, Coriolus hirsutus, Lenzites betulins, Lenzite edodes* and *Pleurotus ostreatus*, the DNA molecule having the structural gene of the desired protein is connected to the DNA molecule permitting expression and secretion can be directly introduced in the cell by the polyethylene glycol method, the electroporation method, particle gun method and the microinjection method, for example. In this case, the convenience with which the recombinant is to be selected is enhanced by having a drug-resistant gene or a nutrition-demanding complementary gene linked to the DNA molecule mentioned above. Further, the efficiency of transformation can be improved by converting the host cell into a protoplast under suitable conditions.

In the present invention, amino acids and polypeptides will be abbreviated in accordance with the method adopted by the Biochemical Committee of IUPAC-IUB. The following abbreviations will be used, for example.

Ala L-alanine
Arg L-arginine
Asn L-asparagine
Asp L-aspartic acid
Cys L-cysteine
Gln L-glutamine
Glu L-glutamic acid
Gly glycin
His L-hist idine
Ile L-isoleucine
Leu L-leucine
Lys L-lysine
Met L-methionine
Phe L-phenylalanine
Pro L-proline
Ser L-sernein
Thr L-threonine
Trp L-tryptophan
Tyr L-tyrosine
Val L-valine The DNA sequences will be abbreviated with the kinds of base contained in the corresponding deoxyribonucleotides forming the sequenes. For example, the following abbreviations will be used.

A Adenine (for deoxyadenylic acid)
C Cytidine (for deoxytidylic acid)
G Guanine (for deoxyguanylic acid)
T Thymine (for deoxythymidylic acid)

This invention provides a DNA for expression and secretion of the gene of protein, particularly the gene of phenoloxidase. This DNA is effective in expressing and secreting the genes of other proteins than the phenoloxidase. This DNA, by being linked with the structural gene of phenoloxidase and introduced into a host organism, provides a novel organism capable of expressing and secreting such proteins as phenoloxidase in an appreciable amount. This invention further provides a method for producing the protein by culturing this novel organism. By this method of production, since the protein such as phenoloxidase is secreted outside the cell bodies of the host microorganism, the intracellular concentrated accumulation of protein harmful to the host can be prevented, the decomposition of product with the intracellular protease precluded, the process of purification of protein heretofore requiring great expenditure of labor and cost simplified, and the cost of production lowered.

EXAMPLE

Now, cloning of DNA molecules concerning expression and secretion of phenoloxidase structural genes and the secretionary expression of proteins will be described in detail below with reference to working examples. It should be noted, however, that this invention is not limited to these working examples.

Example 1

(Synthesis of DNA probe)

The synthesis of a DNA probe was carried out by the amidite method using a DNA synthesizer (produced by Nippon Zeon Co., Ltd. and marketed under trademark designation of "Genet A-III").

The phenoloxidases isolated from three basidiomycetes [*Coriolus hirsutus* IFO 4917, *Coriolus versicolor* IFO 30340, and *Lenzites betulins* IFO 8714] were analyzed by the Edman degradation method to determine their amino acid sequences up to the 25 residues from the N-terminal. The results were as shown below.

First residue at N-terminal

|  | 1 | 2 | 3 | 4 | 5 | 6 | 7 | 8 | 9 | 10 |
|---|---|---|---|---|---|---|---|---|---|---|
| *Coriolus hirsutus* | Ala | -Ile-Gly-Pro- | Thr | -Ala-Asp-Leu-Thr-Ile- |
| *Coriolus virsicolor* | Gly | -Ile-Gly-Pro- | Val | -Ala-Asp-Leu-Thr-Ile- |
| *Lenzites betulins* | Gly | -Ile-Gly-Pro- | Val | -Ala-Asp-Leu-Thr-Ile- |

|  | 11 | 12 | 13 | 14 | 15 | 16 | 17 | 18 | 19 | 20 |
|---|---|---|---|---|---|---|---|---|---|---|
| *Coriolus hirsutus* | Ser | -Asn-Ala- | Glu | -Val-Ser-Pro-Asp-Gly-Phe- |
| *Coriolus virsicolor* | Thr | -Asn-Ala- | Ala | -Val-Ser-Pro-Asp-Gly-Phe- |
| *Lenzites betulins* | Thr | -Asn-Ala- | Glu | -Val-Ser-Pro-Asp-Gly-Phe- |

|  | 21 | 22 | 23 | 24 | 25 |
|---|---|---|---|---|---|
| *Coriolus hirsutus* | Ala-Arg-Gln-Ala-Val- |
| *Coriolus virsicolor* | Ala-Arg-Gln-Ala-Val- |
| *Lenzites betulins* | Ala-Arg-Gln-Ala-Val- |

The following DNA probe was synthesized so as to correspond to the portion of the aforementioned sequence from Pro at the 17th residue to Val at the 25th residue. In the formula, I stands for deoxyinosine.

```
26mer-C (16mix)    3'-CCI-GAC-GGI-TTC-GCI-AGA-CAA-GCI-GT-5'
                          T        T       G   G 26mer-D (8mix)     3'-CCI-GAC-GGI-TTC-GCI-CGI-CAA-GCI-GT-5'
                          T        T       G
```

The phenoloxidases of the three basidiomycetes were decomposed with BrCN and separated by a reverse-phase high-speed liquid chromatographic device [Elution conditions: column (produced by Toyo Soda Manufacturing Co., Ltd. and marketed under trademark designation of "Phenyl-5PW RP"), eluate of concentration gradient from 20% acetonitrile/0.1% TFA to 75% acetonitrile/0.1% TFA, room temperature] to obtain polypeptides. The polypeptides were analyzed by the Edman degradation method to determine amino acid sequences. The results were as shown below.

| | |
|---|---|
| *Coriolus hirsutus* | Met-Ala-Phe-Asn-Phe |
| *Coriolus versicolor* | Met-Ala-Phe-Asn-Phe |
| *Lenzites betulins* | Met-Ala-Phe-Asn-Phe |

The following DNA probe was synthesized so as to correspond to the amino acid sequence mentioned above.

```
15mer-A (16mix)    3'-TAC-CGA-AAA-TTA-AAA-5'
                          T    G   G   G 15mer-B (16mix)    3'-TAC-CGC-AAA-TTA-AAA-5'
                          G    G   G   G
```

From the results indicated above, it is clearly noted that the phenoloxidases produced and secreted by basidiomycetes possess very high degree of homology of amino acid sequences, indicating that DNA's concerning expression and secretion of phenoloxidase genes of all basidiomycetes can be cloned by using the DNA probes used in the present invention. In the following working examples, therefore, methods for cloning DNA molecules concerning expression and secretion of phenoloxidase genes of *Coriolus hirsutus* IFO 4917 will be cited.

Example 2
(Preparation of chromosome DNA)

In an Erlenmeyer flask having an inner volume of 5 liters and containing 1 liter of YPD culture medium (containing yeast extract, 20 g of polypeptone, and 20 g of glucose each per liter), Coriolus hirsutus IFO 4917 was inoculated and shaken cultured at 27° C. for 7 days. After the culture, the cells were collected and frozen in liquefied nitrogen, to obtain about 20 g of frozen cell bodies.

In a mortar, 10 g of frozen cell bodies were ground under liquefied nitrogen for about 15 minutes. In 10 ml of a buffer solution (0.1M NaCl, 0.1M Tris-HCl, 0.1M EDTA, pH 8) kept warmed at 42° C. in advance and containing proteinase K (produced by Boehringer Mannheim-Yamanouchi and marketed under product code of "161519") in a final concentration of 100 $\mu$g/ml, 5 g of the ground cell bodies were gently stirred and left reacting for 2 hours. From the resultant reaction mixture, the chromosomal DNA was extracted with an equal volume of TE (10 mM Tris-HCl, 1 mM EDTA, pH 8) saturated phenol. The extracted chromosomal DNA was precipitated with ethanol, again dissolved in 5 ml of TE, and treated with RNaseA (final concentration 100 $\mu$g/ml; produced by Takara Shuzo Co., Ltd.) at 37° C. for 30 minutes for removal of RNA. The chromosomal DNA was subjected to equilibrium density gradient centrifugal separation (Beckman, Vti80 rotor, 15° C., 50 krpm, 16 hours) using CsCl, to obtain 1.5 mg of refined chromosomal DNA.

Example 3
(Construction of cosmid library of chromosomal DNA)

The amount, 250 $\mu$g, of the refined chromosomal DNA mentioned above and a restriction endonuclease Sau3AI added thereto were subjected to partial decomposition at 37° C. By subjecting the resultant product of partial digestion to a 5 to 25% sucrose density gradient centrifugal separation (Beckman SW40Ti rotor, 15° C., 22.5 krpm, 16 hours), there was obtained about 4 $\mu$g of 32 to 46 Kb chromosomal DNA fragment.

Cosmid vectors were added and a restriction endonuclease BamHI added thereto were left reacting at 37° C. for 12 hours for complete decomposition, and treated with an alkali phosphatase (produced by Takara Shuzo Co., Ltd. and marketed under product code of "2250A") at 37° C. for 30 minutes for removal of phosphoric acid. A mixture of 10 $\mu$g of phenol-extracted cosmid vector and 1 $\mu$g of the 32 to 46 Kb chromosomal DNA fragment was left reacting overnight at 15° C. in the presence of a T4 DNA ligase to effect ligation of the DNA chain.

The resultant product of ligation was subjected to packaging by the use of an in vitro packaging kit produced by Amersham Japan and then infected with an indicating bacterium E. coli DHI. As the result, about 50,000 Ap$^r$ (ampicillin-resistant) strains were obtained and used as a cosmid library of chromosomal DNA.

Example 4
(Cloning of DNA concerning expression and secretion of phenoloxidase structural gene)

About 5,000 clones of recombinant E. coli from the cosmid library were allowed to form colonies on 20 plates of LB agar culture medium containing Ampicillin (final concentration 50 $\mu$g/ml). The colonies were transferred onto two nitrocellulose filters (produced by Amersham Japan K.K.). The filters with the colonies held on the upper sides thereof were placed on filter papers wetted with an alkali solution (1.5M NaCl, 0.5M NaOH) and left standing thereon for 7 minutes. Then, the filters were placed on filter papers wetted with a neutralization solution (1.5M NaCl, 0.5M NaOH) and left standing thereon for 3 minutes. They were then placed on filter papers wetted with a neutral solution and left standing thereon for 3 minutes. The filters were washed twice with SSC (0.3M NaCl, 0.03M trisodium citrate), dried in draft, and treated at 80° C. for 2 hours, to fix the DNA on the filters.

By labelling synthetic DNA probes 15mer-A and B, and 26mer-C and D with radioisotope ($\gamma$-$^{32}$P)ATP (produced by Amersham Japan K.K.) and T4 polynucleotide kinase (produced by Takara Shuzo Co., Ltd. and marketed under product code of "2021A") and hybridizing them with the DNA fixed on the filters, there were obtained clones capable of hybridizing with the two kinds of synthetic DNA probe of 15mer and 26mer, two positive clones of E. coli possessing a cosmid incorporating therein a DNA concerning expression and secretion of a phenoloxidase gene. It is believed that DNA molecules concerning expression and secretion were present in these genes.

For the purpose of restricting the part containing the DNA molecule concerning the expression and secretion of phenoloxidase structural gene in the chromosomal DNA fragment incorporated in the cosmid and sub-cloning the restricted part, the cosmid was sectioned with a restriction endonuclease HindIII, EcoRI or SmaI, separated into fragments by molecular weight by the electrophoresis using 1% of agarose gel, fixed on a filter by the Southern blotting method (Southern, E. M., J. Mol. Biol., 98, 503–517, 1975), and then hybridized with a synthetic DNA probe labelled with $^{32}$p (26mer-C, D and 15mer-A, B). As the result, the two clones were both hybridized, i.e. the 26mer-C, D probes with the DNA fragments of 5.3 Kb of HindIII, 4.6 Kb of EcoRI, and 1.9 Kb of SmaI and the 15mer-A, B probes with the DNA fragments of 5.3 Kb of HindIII, 4.6 Kb of EcoRI, and 2.4 Kb of SmaI.

The DNA fragments were sub-cloned into pUC19 and used for forming a restriction endonuclease physical map. Thus, the two clones were found to possess an identical section pattern (FIG. 1).

Example 5
(Base sequence of DNA concerning expression and secretion of phenoloxidase gene)

The DNA fragments of 4.6 Kb of EcoRI and 5.3 Kb of HindIII obtained by sub-cloning the two clones into plasmid pUC19 was treated with a deletion kit produced by Takara Shuzo Co., Ltd. to form deletion mutants at intervals of 100 to 200 bp, tested with a sequencing kit produced by Takara Shuzo Co., Ltd. to determine the base sequences of DNA's concerning the expression and secretion of the phenoloxidase structural gene originating in the chromosomal DNA and, at the same time, to determine the amino acid sequence (FIGS. 2, 3, 4, and 5).

The EcoRI fragments, i.e. OJ-POG-E1 and OJ-POG-E2, subcloned into pUC vector and concerning expression and secretion have been deposited with Fermentation Research Institute, Agency of Industrial Science and Technology under FERM BP-2793 and FERM BP-2795.

Example 6
(Preparation of mRNA)

In an Erlenmeyer flask having an inner volume of 5 liters and containing 1 liter of a YPD culture medium (10 g of yeast extract, 20 g of polypeptone, and 20 g of glucose each per liter), Coriolus hirsutus IFO 4917 was shaken cultured at 27° C. for 6 days. After the culture broth was confirmed to contain phenoloxidase produced and secreted by the microorganisms, the cells were collected and frozen in liquefied nitrogen. Consequently, there were obtained about 20 g of frozen cell bodies.

From 5 g of the frozen cell bodies, 11 mg of total mRNA was extracted by Broda et al's method. Specifically, this recovery of 11 mg of total mRNA was effected by grinding 5 g of frozen cell bodies in a 100-ml whirling blender containing nitrogen, dissolving the ground cell bodies in 3 times as large in volume of a TNS buffer solution (1% triisopropylnaphthalenesulfonic acid, 200 mM Tris-HCl, 25 mM EDTA (pH 7.8), 250 mM NaCl), centrifuging the resultant solution for expulsion of pellets, adding to the supernatant 0.5 g of phenol per ml of the supernatant, keeping the supernatant at temperature of 50 to 15° C. for further solution and, after the whole phenol was dissolved, adding to the solution one half in volume of chloroform, centrifuging and recovering the supernatant, extracting the supernatant twice from chloroform, and treating with ethanol to induce precipitation.

When the extraction was carried out by the use of a commercially available mRNA extraction kit (produced by Amersham Japan K.K.), 6.7 mg of total mRNA was obtained from 3 g of frozen cell bodies.

The total mRNA recovered by the two methods described above was confirmed to contain the mRNA originating from the phenoloxidase gene by the Nothern; blot hybridization method [Thomas, P. S., Proc. Natl. Acad. Sci. USA 77, 5201 (1980)] using the DNA probe of phenoloxidase.

By Maniatis et al's method (Maniatis et al, Molecular Cloning, Laboratory Manual, 197–199, 1982) using cellulose oligo(dt) column, 5 mg of the total mRNA was treated to isolate poly(A)mRNA. Consequently, there was obtained about 100 μg purified of poly(A)mRNA.

Example 7
(Synthesis of cDNA)

The synthesis of cDNA from th e poly(A)mRNA originating in the white-rot fungus (Coriolus hirsutus IFO 4917) was carried out by the Gulber and Hoffman's method [U. Gubler & B. J. Hoffman; Gene, 25, 263–269 (1983)] using a cDNA synthesizing kit made by Amersham Japan K.K.

By adding to 5 μg of poly(A)mRNA 5 μg of 011go(dT) 12–18 (produced by Pharmacia and marketed under product code of "27-7858-01") in the presence of 50 units of RNAse inhibiting enzyme (HPRI) originating in human fetus and causing 100 units of a reverse transcriptase to react on the resultant mixture at 42° C. for 1.5 hours, there was synthesized a single-chain cDNA in a yield of about 30%. The reaction solution thus obtained and 4 units of E. coli ribonuclease H and 115 units of E. coli DNA polymerase I added thereto were left reacting at 12° C. for 1 hour and at 22° C. for 1 hour and thereafter left standing at 70° C. for 10 minutes to inactivate the enzyme. The reaction solution thus obtained and 10 units of T4 DNA polymerase added thereto were left reacting at 37° C. for 10 minutes, to obtain a two-chain cDNA in a yield of about 95%.

Example 8
(Construction of cDNA library)

A cDNA library was constructed with a commercially available λgt11 cloning system (produced by Amersham Japan K.K.).

One hundred (100) μg of the two-chain cDNA and 20 units of EcoRI methylase were left reacting at 37° C. for 1 hour and a EcoRI linker was ligated thereto. The resultant reaction solution and 16 units of EcoRI added thereto were left reacting at 37° C. for 2 hours and then passed through a Sepharose CL-4B column for purification. The resultant reaction product was subjected to a linking reaction with 1 μg of λgt11 arm and then to in vitro packaging [A. Becker & M. Gold; Proc. Natl. Acad. Sci. USA, 72, 581 (1975)], to obtain $10^6$ recombinant λ phage bodies. With the phage bodies, a cDNA library originating in the mRNA of Coriolus hirsutus IFO 4917 was obtained.

Example 9
(Cloning of DNA concerning upstream secretion of phenoloxidase structural gene originating in mRNA)

The cDNA library originating in the mRNA of Coriolus hirsutus IFO 4917 obtained in Example 4 was caused to infect an E. coli Y 1090 strain and form a plaque.

The clone containing the DNA concerning the upstream secretion of the phenoloxidase structural gene originating in the mRNA, similarly to the cloning of the DNA concerning the expression and secretion of the phenoloxidase structural gene originating in the chromosomal DNA, was treated by the Benton and Davis's plaque hybridization method [W. D.

Benton & R. W. Davis; Science, 196, 180 (1977)] using a DNA probe labelled with a radioisotope to separate two clones.

The isolation of a purified DNA from the λgt11 phage containing the phenoloxidase structural gene originating in the mRNA and the upstream DNA molecule concerning secretion of the gene was carried out by Thomas and Davis's method [M. Thomas & R. W. Davis: Journal of Molecular Biology, 91, 315 (1974)].

Example 10

(Determination of base sequence of the DNA molecule concerning upstream secretion of phenoloxidase structural gene originating in mRNA)

The two clone λgt11 DNA's containing the phenoloxidase gene originating in the mRNA and the DNA concerning the secretion thereof obtained in Example 9 were sectioned with a restriction endonuclease EcoRI to cut off the inserted phenoloxidase gene and then given sub-cloning at the sites of plasmid vector pUC19 and pUC118.

The clone obtained by sub-cloning at the site of pUC19 was designated as OJ-POM 5 and the clone obtained by sub-cloning at the site of pUC118 as OJ-POM 2.

A restriction endonuclease section map of the sub-cloned cDNA was produced by the conventional method. This map is shown in FIG. 6.

The restriction endonuclease maps of OJ-POM 5 and OJ-POM 2 were identical to each other.

Similarly to the sequence of the DNA molecule concerning the expression and secretion of the phenoloxidase structural gene originating in the chromosome, the sub-cloned cDNA was treated with a commercially available deletion kit (produced by Takara Shuzo Co., Ltd.) to form a deletion mutant and then treated by the dideoxy method using a commercially available M13 sequencing kit (produced by Takara Shuzo Co., Ltd.) to determine the base sequence of the DNA concerning the secretion of the phenoloxidase gene originating in the mRNA. At the same time, the total amino acid sequence of the phenoloxidase was determined.

The DNA concerning the secretion of the structural gene was found to be perfectly in agreement with the region concerning the secretion of the chromosome illustrated in FIGS. 2 and 3 and was found to contain part of the region concerning expression.

Example 11

(Secretionary expression with yeast)

Figure 8:
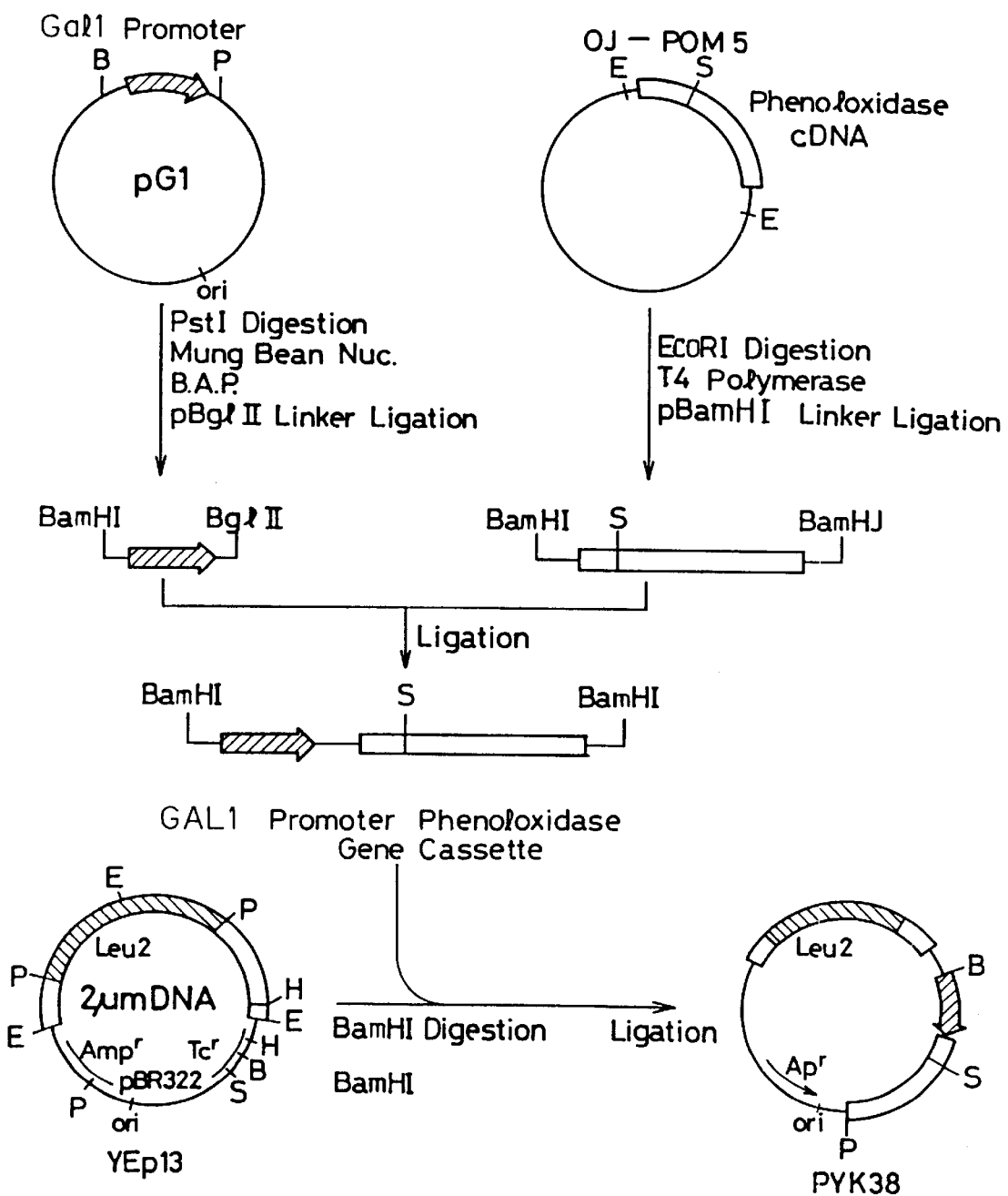
FIG. 8 is the construction of a plasmid by the use of the DNA concerning the secretion of the phenoloxidase gene.

A plasmid having the DNA molecule concerning secretion originating in the mRNA and the phenoloxidase structural gene linked to the downstream of the promotor GAL1 of yeast (pG1: ATCC 37305) was constructed as illustrated in FIG. 8. The transformed organism SCSHY3/pYK38 containing pYK38 has been deposited with Fermentation Research Institute, Agency of Industrial Science and Technology under FERM BP-2794.

The yeast SHY3 transformed with the plasmid was cultured in a glucose culture medium and in a galactose culture medium. In the glucose culture medium, no phenoloxidase was detected in either the culture medium or the cells. In the galactose culture medium, phenoloxidase was secretionarily produced in an amount of 5 μg/ml in the culture medium. The results evince that the DNA molecule concerning secretion originating in the mRNA can be similarly utilizable in the yeast and that it fulfils the secretionary effect and is utilizable in the presence of a yeast promoter capable of ON-OFF control.

Example 12

(Secretionary manifestation with Coriolus hirsutus IFO 4917)

Figure 7:
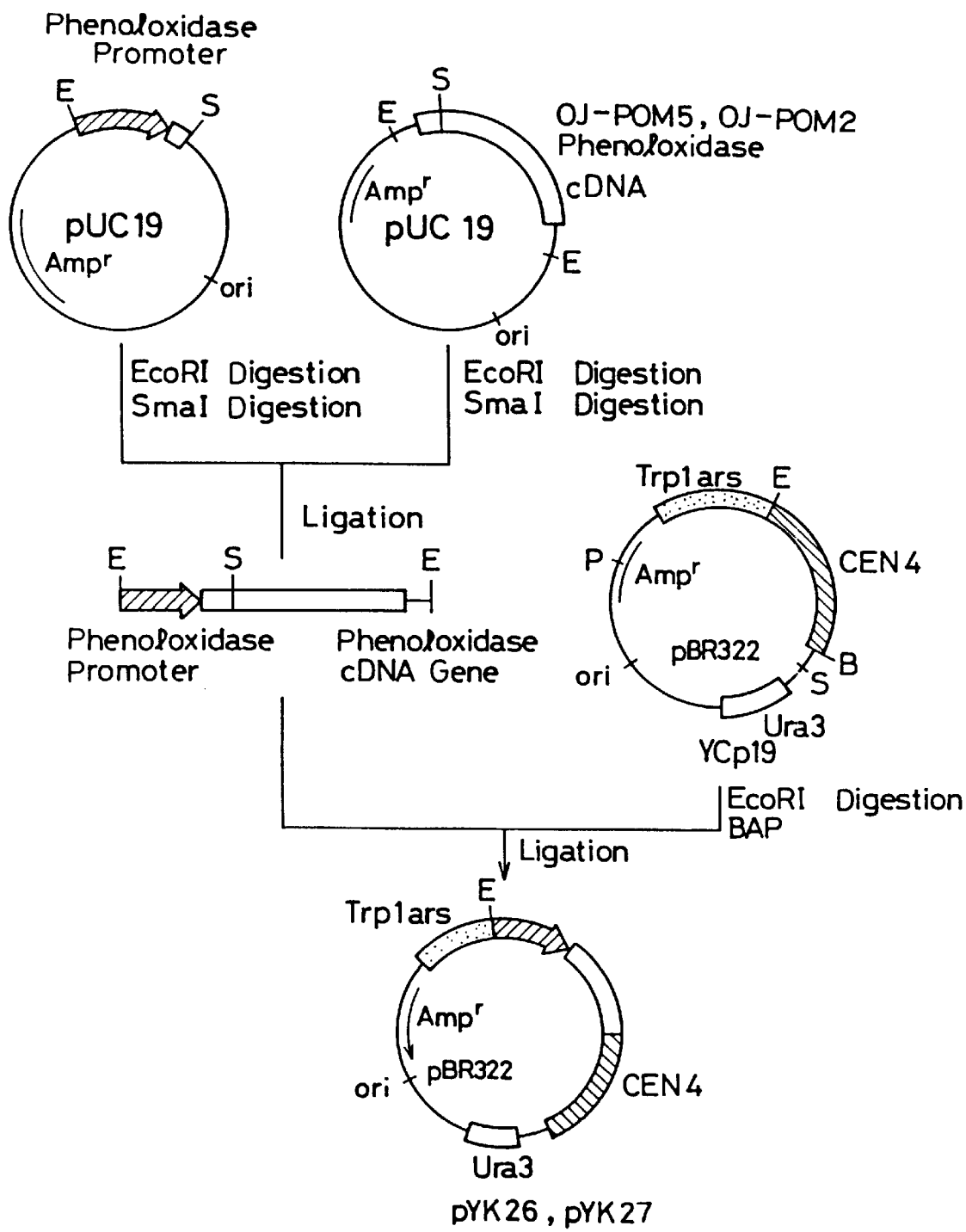
FIG. 7 is the construction of two plasmids containing the DNA concerning expression and secretion of the phenoloxidase gene. OJ-POM2 and OJ-POM5 (see Example 10 on page 45) were each ligated to the yeast YCp19 vector to form, respectively, the pYK26 and pYK27 plasmid vectors.

A phenoloxidase gene EcoRI fragment possessing a DNA concerning expression and secretion originating in a chromosome (FIG. 1) or a phenoloxidase gene cassette produced as shown in FIG. 7 were independently or jointly incorporated in pUC19 and YCp19 vectors and introduced into a protoplast of Coriolus hirsutus IFO 4917 by the electroporation method (P. K. Howard et al, Nucleic Acid Research, Vol. 16, 2613–2623). The resultant products were scattered on plates. The colonies consequently formed were isolated and subjected to liquid culture. Consequently, there were obtained clones having the phenoloxidase activity enhanced to several times the original level.

The chromosomal DNA were extracted from the clones possessed of enhanced phenoloxidase activity and subjected to the Southern hybridization using a phenoloxidase gene to confirm that several copies of phenoloxidase gene were incorporated on the chromosome.

The results are believed to imply that the secretionary production of phenoloxidase was increased by the amplification of the gene. Thus, it has been demonstrated that the DNA concerning the expression and secretion of the cloned phenoloxidase gene can be effectively utilized in basidiomycetes.

Various references are cited herein, the disclosures of which in their entireties are incorporated herein by reference.

What is claimed is:

1. A DNA consisting essentially of the sequence described in FIG. 2.

2. A DNA consisting essentially of the sequence described in FIG. 3.

3. A DNA consisting essentially of the sequence described in FIG. 4.

4. A DNA consisting essentially of the sequence described in FIG. 5.

5. A recombinant vector comprising DNA I or II in operable linkage 5' to the structural gene for phenoloxidase and DNA III or IV in operable linkage 3' to said structural gene, wherein said DNA I, II, III or IV has the sequence described in FIGS. 2, 3, 4 or 5, respectively.

6. A recombinant vector comprising a yeast GAL promoter linked to a basidiomycetes-derived signal peptide gene sequence which is linked in turn to the structural gene for phenoloxidase of Coriolus hirsutus.

7. A plasmid pYK38 which is contained in Saccharomyces cerevisiae SHY3 (Accession Number: FERM BP-2794).

8. A yeast host transformed with the vector of claim 5 and capable of producing enhanced amounts of phenoloxidase.

9. The yeast host of claim 8 being Saccharomyces cerevisiae.

10. A yeast host transformed with the plasmid of claim 7.

11. The yeast host of claim 10 which is Saccharomyces cerevisiae.

12. The yeast host of claim 11 which is Saccharomyces cerevisiae SHY3 containing pYK38 (Accession Number: FERM BP-2794).

13. A basidiomycete host transformed with the vector of claim 5 and capable of producing enhanced amounts of phenoloxidase.

14. The basidiomycete host of claim 13 which is Coriolus hirsutus.

* * * * *